(12) United States Patent
Glide-Hurst et al.

(10) Patent No.: US 8,870,771 B2
(45) Date of Patent: Oct. 28, 2014

(54) METHOD AND APPARATUS FOR CATEGORIZING BREAST DENSITY AND ASSESSING CANCER RISK UTILIZING ACOUSTIC PARAMETERS

(75) Inventors: Carri K. Glide-Hurst, Mt. Clemens, MI (US); Nebojsa Duric, Bloomfield Hills, MI (US); Peter J. Littrup, Bloomfield Hills, MI (US)

(73) Assignee: Barbara Ann Karmanos Cancer Institute, Detroit, MI (US)

( * ) Notice: Subject to any disclaimer, the term of this patent is extended or adjusted under 35 U.S.C. 154(b) by 1030 days.

(21) Appl. No.: 12/115,174

(22) Filed: May 5, 2008

(65) Prior Publication Data

US 2008/0275344 A1 Nov. 6, 2008

Related U.S. Application Data

(60) Provisional application No. 60/915,946, filed on May 4, 2007.

(51) Int. Cl.
*A61B 8/00* (2006.01)
*A61B 8/08* (2006.01)
(52) U.S. Cl.
CPC .................................. *A61B 8/0825* (2013.01)
USPC ....................................................... 600/438
(58) Field of Classification Search
USPC ............. 600/438, 442, 437; 73/596, 597, 599
See application file for complete search history.

(56) References Cited

U.S. PATENT DOCUMENTS

| | | |
|---|---|---|
| 3,154,067 A | 10/1964 | Stenstrom et al. |
| 3,881,466 A | 5/1975 | Wilcox |
| 3,886,489 A | 5/1975 | Jones |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,222,274 A | 9/1980 | Johnson |
| 4,317,369 A | 3/1982 | Johnson |
| 4,328,707 A | 5/1982 | Clement et al. |
| 4,433,690 A | 2/1984 | Green et al. |
| 4,509,368 A | 4/1985 | Whiting et al. |
| 4,515,165 A | 5/1985 | Carroll |
| 4,541,436 A | 9/1985 | Hassler et al. |
| 4,542,744 A | 9/1985 | Barnes et al. |

(Continued)

FOREIGN PATENT DOCUMENTS

| | | |
|---|---|---|
| CA | 2324602 A | 9/1999 |
| EP | 284055 A | 9/1988 |

(Continued)

OTHER PUBLICATIONS

Chang et al., Breast Density Analysis in 3-D Whole Breast Ultrasound Images, 2006, IEEE, Proceedings of the 28th IEEE EMBS annual International Conference, 2795-2798.*

(Continued)

*Primary Examiner* — Elmer Chao
(74) *Attorney, Agent, or Firm* — Jeffrey Schox

(57) ABSTRACT

A method for categorizing whole-breast density is disclosed. The method includes the steps of exposing breast tissue to an acoustic signal; measuring a distribution of an acoustic parameter by analyzing the acoustic signal; and obtaining a measure of whole-breast density from said measuring step. An apparatus is also disclosed.

26 Claims, 6 Drawing Sheets

(56) References Cited

U.S. PATENT DOCUMENTS

| | | | |
|---|---|---|---|
| 4,562,540 A | 12/1985 | Devaney |
| 4,564,019 A | 1/1986 | Miwa |
| 4,646,756 A | 3/1987 | Watmough et al. |
| 4,662,222 A | 5/1987 | Johnson |
| 4,671,256 A | 6/1987 | Lemelson |
| 4,855,911 A | 8/1989 | Lele et al. |
| 4,858,124 A | 8/1989 | Lizzi et al. |
| 4,917,096 A | 4/1990 | Englehart et al. |
| 4,941,474 A | 7/1990 | Pratt, Jr. |
| 5,003,979 A | 4/1991 | Merickel et al. |
| 5,029,476 A | 7/1991 | Metala et al. |
| RE33,672 E | 8/1991 | Miwa |
| 5,095,909 A | 3/1992 | Nakayama et al. |
| 5,143,069 A | 9/1992 | Kwon et al. |
| 5,158,071 A | 10/1992 | Umemura et al. |
| 5,178,147 A | 1/1993 | Ophir et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,268,876 A | 12/1993 | Rachlin |
| 5,269,309 A | 12/1993 | Fort et al. |
| 5,280,788 A | 1/1994 | Janes et al. |
| 5,304,173 A | 4/1994 | Kittrell et al. |
| 5,305,752 A | 4/1994 | Spivey et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,413,108 A | 5/1995 | Alfano |
| 5,415,164 A | 5/1995 | Faupel et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,546,945 A * | 8/1996 | Soldner | 600/448 |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,590,653 A | 1/1997 | Aida et al. |
| 5,596,992 A | 1/1997 | Haaland et al. |
| 5,606,971 A | 3/1997 | Sarvazyan |
| 5,609,152 A | 3/1997 | Pellegrino et al. |
| 5,620,479 A | 4/1997 | Diederich |
| 5,640,956 A | 6/1997 | Getzinger et al. |
| 5,643,179 A | 7/1997 | Fujimoto |
| 5,664,573 A | 9/1997 | Shmulewitz |
| 5,678,565 A | 10/1997 | Sarvazyan |
| 5,722,411 A | 3/1998 | Suzuki et al. |
| 5,743,863 A | 4/1998 | Chapelon |
| 5,749,364 A | 5/1998 | Sliwa, Jr. et al. |
| 5,759,162 A | 6/1998 | Oppelt et al. |
| 5,762,066 A | 6/1998 | Law et al. |
| 5,766,129 A | 6/1998 | Mochizuki |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,833,614 A | 11/1998 | Dodd et al. |
| 5,846,202 A | 12/1998 | Ramamurthy et al. |
| 5,855,554 A | 1/1999 | Schneider et al. |
| 5,865,167 A | 2/1999 | Godik |
| 5,865,743 A | 2/1999 | Godik |
| 5,891,619 A | 4/1999 | Zakim et al. |
| 6,002,958 A | 12/1999 | Godik |
| 6,005,916 A | 12/1999 | Johnson et al. |
| 6,023,632 A | 2/2000 | Wilk |
| 6,050,943 A | 4/2000 | Slayton et al. |
| 6,056,690 A * | 5/2000 | Roberts | 600/300 |
| 6,083,166 A * | 7/2000 | Holdaway et al. | 600/439 |
| 6,102,857 A | 8/2000 | Kruger |
| 6,109,270 A | 8/2000 | Mah et al. |
| 6,117,080 A | 9/2000 | Schwartz |
| 6,135,960 A | 10/2000 | Holmberg |
| 6,149,441 A | 11/2000 | Pellegrino et al. |
| 6,242,472 B1 | 6/2001 | Sekins et al. |
| 6,289,235 B1 | 9/2001 | Webber et al. |
| 6,292,682 B1 | 9/2001 | Kruger |
| 6,296,489 B1 | 10/2001 | Blass et al. |
| 6,317,617 B1 | 11/2001 | Gilhuijs et al. |
| 6,368,275 B1 | 4/2002 | Sliwa et al. |
| 6,385,474 B1 | 5/2002 | Rather et al. |
| 6,413,219 B1 | 7/2002 | Avila et al. |
| 6,450,960 B1 | 9/2002 | Rather et al. |
| 6,475,150 B2 | 11/2002 | Haddad |
| 6,478,739 B1 | 11/2002 | Hong |
| 6,490,469 B2 | 12/2002 | Candy |
| 6,511,427 B1 | 1/2003 | Sliwa, Jr. et al. |
| 6,527,759 B1 | 3/2003 | Tachibana et al. |
| 6,540,678 B2 | 4/2003 | Rather et al. |
| 6,559,178 B1 | 5/2003 | Zamoyski |
| 6,587,540 B1 * | 7/2003 | Johnson et al. | 378/62 |
| 6,636,584 B2 | 10/2003 | Johnson et al. |
| 6,645,202 B1 | 11/2003 | Pless et al. |
| 6,672,165 B2 | 1/2004 | Rather et al. |
| 6,716,412 B2 | 4/2004 | Unger |
| 6,728,567 B2 | 4/2004 | Rather et al. |
| 6,776,760 B2 | 8/2004 | Marmarelis |
| 6,785,570 B2 | 8/2004 | Nir |
| 6,810,278 B2 | 10/2004 | Webber et al. |
| 6,837,854 B2 | 1/2005 | Moore et al. |
| 6,883,194 B2 | 4/2005 | Corbeil et al. |
| 6,926,672 B2 | 8/2005 | Moore et al. |
| 6,939,301 B2 | 9/2005 | Abdelhak |
| 6,984,210 B2 | 1/2006 | Chambers et al. |
| 7,025,725 B2 * | 4/2006 | Dione et al. | 600/443 |
| 7,179,449 B2 | 2/2007 | Lanza et al. |
| 7,285,092 B2 | 10/2007 | Duric et al. |
| 7,346,203 B2 | 3/2008 | Turek et al. |
| 7,497,830 B2 | 3/2009 | Li |
| 7,530,951 B2 | 5/2009 | Fehre et al. |
| 7,556,602 B2 | 7/2009 | Wang et al. |
| 7,570,742 B2 | 8/2009 | Johnson et al. |
| 2001/0029334 A1 | 10/2001 | Graumann et al. |
| 2001/0037075 A1 | 11/2001 | Candy |
| 2002/0065466 A1 | 5/2002 | Rather et al. |
| 2002/0099290 A1 | 7/2002 | Haddad |
| 2002/0131551 A1 | 9/2002 | Johnson et al. |
| 2003/0138053 A1 | 7/2003 | Candy et al. |
| 2004/0030227 A1 | 2/2004 | Littrup et al. |
| 2004/0059265 A1 | 3/2004 | Candy et al. |
| 2004/0167396 A1 | 8/2004 | Chambers et al. |
| 2004/0181154 A1 * | 9/2004 | Peterson et al. | 600/459 |
| 2005/0260745 A1 | 11/2005 | Domansky et al. |
| 2006/0009693 A1 | 1/2006 | Hanover et al. |
| 2006/0020205 A1 | 1/2006 | Kamiyama |
| 2006/0064014 A1 | 3/2006 | Falco et al. |
| 2006/0085049 A1 | 4/2006 | Cory et al. |
| 2006/0287596 A1 | 12/2006 | Johnson et al. |
| 2006/0293597 A1 | 12/2006 | Johnson et al. |
| 2008/0045864 A1 * | 2/2008 | Candy et al. | 601/2 |
| 2008/0218743 A1 | 9/2008 | Stetten et al. |
| 2008/0229832 A1 | 9/2008 | Huang et al. |
| 2008/0269812 A1 | 10/2008 | Gerber et al. |
| 2008/0275344 A1 | 11/2008 | Glide-Hurst et al. |
| 2008/0281205 A1 | 11/2008 | Naghavi et al. |
| 2008/0294027 A1 | 11/2008 | Frinking et al. |
| 2008/0294043 A1 | 11/2008 | Johnson et al. |
| 2008/0319318 A1 | 12/2008 | Johnson et al. |
| 2009/0035218 A1 | 2/2009 | Ross et al. |
| 2009/0143674 A1 | 6/2009 | Nields et al. |
| 2010/0331699 A1 | 12/2010 | Yu et al. |

FOREIGN PATENT DOCUMENTS

| | | |
|---|---|---|
| EP | 351610 A | 1/1990 |
| EP | 538241 A | 4/1993 |
| EP | 609922 A | 8/1994 |
| EP | 661029 A | 7/1995 |

(56) References Cited

FOREIGN PATENT DOCUMENTS

| | | |
|---|---|---|
| EP | 774276 A | 5/1997 |
| EP | 1063920 A | 1/2001 |
| JP | 2005253827 A | 9/2005 |
| JP | 2007181679 A | 7/2007 |
| JP | 2009034521 A | 2/2009 |
| WO | 9947046 A | 9/1999 |
| WO | 0228350 | 4/2002 |
| WO | 0230288 A | 4/2002 |
| WO | 2004061743 A | 7/2004 |
| WO | 2005057467 A | 6/2005 |
| WO | 2007023408 A | 3/2007 |

OTHER PUBLICATIONS

U.S. Appl. No. 60/901,903, filed Feb. 16, 2007, Li et al.
*Prospective Breast Cancer Risk Prediction Model for Women Undergoing Screening Mammography*; William E. Barlow et al, Journal of the National Cancer Institute, vol. 98, No. 17, Sep. 6, 2006.
Projecting Absolute Invasive Breast Cancer Risk in White Women With a Model that Includes Mammographic Density; Jinbo Chen et al, Journal of the National Cancer institute, vol. 98, No. 17, Sep. 6, 2006.
Longitudinal Measurement of Clinical Mammographic Breast Density to Improve Estimation of Breast Cancer Risk; Karla Kerlikowske et al, Journal of the National Cancer Institute, vol. 99, Issue 5, Mar. 7, 2007.
Mammographic Density Correlation with Gail Model Breast Cancer Risk Estimates and Component Risk Factors; Melanie R. Palomares et al, Cancer Epidemiol Biomarkers Prev 2006; 15(7), Jul. 2006.
*The Ultrasonic Field as a Medical Tool*; Dussik, K., American Journal of Physical Medicine, Vo. 33, Issue 1, Feb. 1954.
*Computerized Tomography With Ultrasound*; James Greenleaf, Proceedings of the IEEE, vo. 71, No. 3, Mar. 1983.
Elastography: Ultrasonic Estimation and Imaging of the Elastic Properties of Tissues; J. Ophir et al, Proc Instn Mech Engrs, vol. 213 Part H, pp. 203-233.
*Volumetric Imaging with Ultrasonic Spiral CT*; Haim Azhari et al, Dept. of Biomedical Engineering Technion, Israel Institute of Technology, 1999, pp. 270-275.
*Ultrasonographically Defined Parenchymal Patters of the Breast*; L. Kaizer et al, The British Journal of Radiology, vol. 61, Issue 722, Feb. 1988, pp. 118-124.
*A New Method of Measuring in Vivo Sound Speed in the Reflection Mode*; N. Hayashi, Journal of Clinical Ultrasound, vol. 16, Issue 2, Feb. 1988, pp. 87-93.
*Velocity Compensation in Water-Coupled Breast Echography*; J. Jellins et al, Ultrasonics, vol. 11, Issue 5, 1973, pp. 223-226.
Automated Classification of Parenchymal Patterns in Mammograms; N. Karssemeijer, Phys. Med. Biol. 43 (1998) 365-378.
*Average Velocity of Ultrasound in the Human Female Breast*; George Kossoff et al, The Journal of the Acoustical Society of America, vol. 53, Issue 6, Jul. 1973, pp. 1730-1736.
Empirical Relationships Between Acoustic Parameters in Human Soft Tissues; T. Douglas Mast, Acoustics Research Letters Online, Nov. 16, 2000.
Relationship Between Myocardial Tissue Density Measured by Microgravimetry and Sound Speed Measured by Acoustic Microscopy; H. Masugata et al, Ultrasound in Med. & Biol. vol. 25, No. 9, pp. 1459-1463, 1999.
*Quantitative Sonography*; D.E. Robinson et al, Ultrasound in Medicine & Biology, vol. 12, Issue 7, Jul. 1986, pp. 555-565.
*Direct Measurement of Sound Velocity in Various Specimens of Breast Tissue*; Wieland Weiwad et al, Investigative Radiology, vol. 35, Issue 12, 2000, pp. 721-726.
*Comparative Studies of Various Echomammography*; J. Teubner et al, Ultraschall in Der Medizin, Sep. 1982, 3(3):109-18.
*Dedicated Breast CT: Radiation Dose and Image Quality Evaluation*; John Boone et al, Medical Physics, vol. 221, No. 3, Dec. 2001, pp. 657-667.

Estimation of the Content of Fat and Parenchyma in Breast Tissue Using MRI $T_1$ Histograms and Phantoms; Raymond Boston et al, Magnetic Resonance Imaging 23 (2005) 591-599.
Quantitative Classification of Mammographic Densities and Breast Cancer Risk: Results From the Canadian National Breast Screening Study; N.F. Boyd, Journal of the National Cancer Institute, vol. 87, No. 9, May 3, 1995.
*The Quantitative Analysis of Mammographic Densities*; J.W. Byng et al, Phys. Med. Biol. 39 (1994) 1629-1638.
Automatic Labelling and BI-RADS Characterisation of Mammogram Densities; K. Marias, Proceedings of the 2005 IEEE, Sep. 1-4, 2005, pp. 6394-6398.
Correlation Between Mammographic Density and Volumetric Fibroglandular Tissue Estimated on Breast MR Images; Jun Wei et al, Medical Physics, vol. 31, No. 4, Apr. 2004.
Risk for Breast Cancer Development Determined by Mammographic Parenchymal Pattern; John N. Wolfe, Cancer, vol. 37, Issue 5, May 1976.
*Breat Cancer Risk and Measured Mammographic Density*; M.J. Yaffe, European Journal of Cancer Prevention, vol. 7 Suppl 1, 1998, pp. S47-S55.
Detection of Breast Cancer With Ultrasound Tomography: First Results With the Computed Ultrasound Risk Evaluation (CURE) Prototype; Nebojsa Duric et al, Medical Physics, vol. 34, No. 2, Feb. 2007.
Novel Approach to Evaluating Breast Density Utilizing Ultrasound Tomography; Carri Glide et al, Medical Physics, vol. 34, No. 2, Feb. 2007.
*A New Method for Quantitative Analysis of Mammographic Density*; Carri K. Glide-Hurst, Medical Physics, vol. 34, No. 11, Nov. 2007.
*A Novel Ultrasonic Method for Measuring Breast Density and Breast Cancer Risk*; Carri K. Glide-Hurst et al; Medical Imaging 2008, Proc. of SPIE vol. 6920, 69200Q.
Clinical Breast Imaging Using Sound-Speed Reconstructions of Ultrasound Tomography Data; Cuiping Li et al; Medical Imaging 2008, Proc. of SPIE vol. 6920, 6920009.
*A Novel Approach to Evaluating Breast Density Using Ultrasound Tomography*; Carri K. Glide, Dissertation Graduate School of Wayne State University, 2007.
Breast Density Analysis in 3-D Whole Breast Ultrasound Images, Proceedings of the 28th IEEE EMBS Annual International conference, New York City, USA, Aug. 30-Sep. 3, 2006, pp. 2795-2798.
Metz, "Basic principles of ROC analysis"; Semin Nucl Med. Oct. 8, 1978 (4):283-98.
Metz, "Receiver Operating Characteristic Analysis: A Tool for the Quantitative Evaluation of Observer Performance and Imaging Systems"; J Am Coli Radiol 2006; 3: 413-422.
Metz, "ROC methodology in radiologic imaging"; Invest Radiol. Sep. 21, 1986 (9):720-33.
Chang et al., Kirchhoff migration of ultrasonic images, Materials evaluation, V59, N3, 413-417, 2001.
Klimes, Grid Travel-time Tracing: Second-order Method for the First Arrivals in Smooth Media, PAGEOPH, vol. 148, Nos. 3/4,1996.
Li et al., Breast Imaging Using Transmission Ultrasound: Reconstructing Tissue Parameters of Sound Speed and Attenuation,2008 International Conference on BioMedical Engineering and Informatics, IEEE computer society, 708-712.
Li et al., Comparison of ultrasound attenuation tomography methods for breast imaging, Medical Imaging 2008: UltrasonicImaging and Signal Processing, Proc. of SPIE vol. 6920, 692015-(1-9), 2008.
Li et al., Refraction corrected transmission ultrasound computed tomography for application in breast imaging, Med. Phys. 37(5), May 2010, 2233-2246.
Walach et al., Local Tissue Attenuation Images Based on Pulsed-Echo Ultrasound Scans, IEEE Transactions Onbiomedical Engineering, vol. 36. No. 2, Feb. 1989.
Duric et al. "Computed Ultrasound Risk Evaluation," Barbara Ann Karmanos Cancer Institute. pp. 1-23. 2008.
Xu, et al. "A Study of 3-Way Image Fusion for Characterizing Acoustic Properties of Breast Tissue." Medical Imaging 2008: Ultrasonic Imaging and Signal Processing. Feb. 16, 2008.
Centerline, PortalVision section, Summer 2002 edition, published by Varian Medical Systems.

(56) References Cited

OTHER PUBLICATIONS

Chelfouh et al., "Characterization of Urinary Calculi: in Vitro Study of 'Twinking Artifact' revealed by Color-Flow Sonography," AJR Am. J. Roentgenol. 171(4) (1998) 1055-60.

Diederich et al., "The design of ultrasound applicators for interstitial hyperthermia," Ultrasonics Symposium, Proc IEEE 1993 Baltimore, MD, USA Oct. 31-Nov. 3, 1993, New York, NY, USA, 1215-1219.

Fjield et al., "A Parametric Study of the Concentric-Ring Transducer Design for MRI Guided Ultrasound Surgery," J Acoust. Soc. America 100 (2) Pt. 1 (1996).

Gervias et al., "Renal Cell Carcinoma: Clinical Experience and Technical Success with Radio-frequency Ablation of 42 Tumors," Radiology 226 (2003) 417-424.

Greenleaf et al., "Artificial Cavitation Nuclei Significantly Enhance Acoustically Incuded Cell Transfection," Ultrasound Med & Biol 24 (1998) 587-595.

Louvar et al., "Correlation of Color Doppler Flow in the Prostate with Tissue Microvascularity," Cancer 1:83(1) (1998) 135-40.

Miller et al., "Sonoporation of Cultured Cells in the Rotating Tube Exposure System," Ultrasound Med & Biol 25 (1999) 143-149.

Noble et al., "Spleen Hemostasis Using High-Intensity Ultrasound: Survival and Healing," J. Trauma Injury, Infection, and Critical Care 53(6) (2002) 1115-1120.

Vaezy et al., "Real-Time Visualization of High-Intensity Focused Ultrasound Treatment Using Ultrasound Imaging," Ultrasound in Med & Biol 27(1) (2001) 33-42.

Yankelevitz et al., "Small Pulmonary Nodules: Volumetrically Determined Growth Rates Based on CT Evaluation," Radiology 217 (2000) 251-256.

Banihashemi, B. et al., "Ultrasound Imaging of Apoptosis in Tumor Response: Novel Preclinical Monitoring of Photodynamic Therapy Effects." Cancer Research, vol. 68, No. 20, Oct. 15, 2008, pp. 8590-8596.

Singh, Seema et al. "Color Doppler Ultrasound as an Objective Assessment Tool for Chemotherapeutic Response in Advanced Breast Cancer." Breast Cancer, 2005, vol. 12, No. 1, 2005, pp. 45-51.

Yaman, C. et al., "Three-Dimensional Ultrasound to Assess the Response to Treatment in Gynecological Malignancies." Gynecologic Oncology, Academic Press, vol. 97, No. 2, May 1, 2005, pp. 665-668.

Glide-Hurst et al., "Volumetric breast density evaluation from ultrasound tomography images", Medical Physics, vol. 35, 2008, pp. 3988-3997.

Li et al., "In Vivo Breast Sound-Speed Imaging with Ultrasound Tomography", Ultrasound in Med & Bioi., vol. 35, No. 10, 2009, pp. 1615-1628.

* cited by examiner

Fatty  Scattered  Heterogeneous  Dense

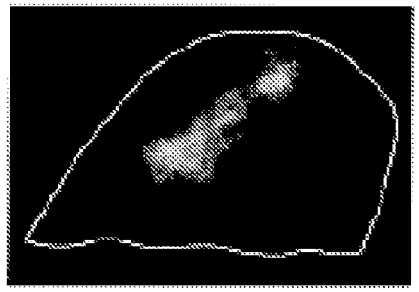
*FIG. 8C*
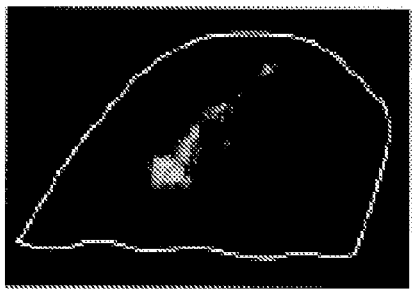
*FIG. 8G*
*FIG. 8B*
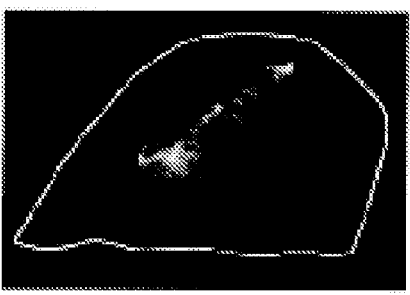
*FIG. 8F*
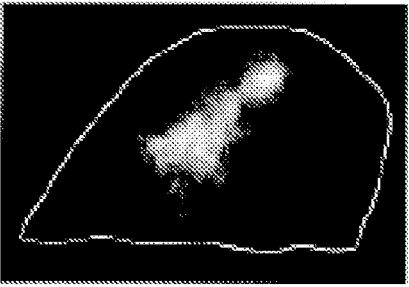
*FIG. 8A*
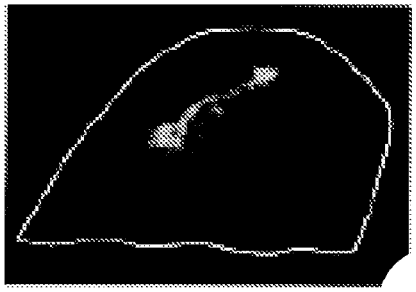
*FIG. 8E*
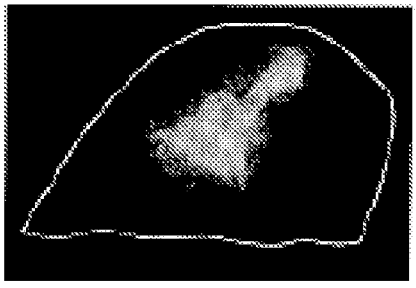

METHOD AND APPARATUS FOR CATEGORIZING BREAST DENSITY AND ASSESSING CANCER RISK UTILIZING ACOUSTIC PARAMETERS

RELATED APPLICATION

This disclosure claims the benefit of Provisional Patent Application No. 60/915,946, filed on May 4, 2007.

FIELD OF THE INVENTION

The disclosure relates to medical devices and more particularly relates to a method and apparatus for determining breast density and assessing cancer risk utilizing acoustic parameters.

DESCRIPTION OF THE RELATED ART

According to the World Health Organization, breast cancer is the second most common type of cancer and the fifth most common cause of cancer death. In view of the commonality of breast cancer, diligent individuals subject themselves to regular mammograms for the purpose of detecting an existence of breast cancer.

An ancillary benefit of having a mammogram conducted is the ability of the radiologist to determine a radiographical density of the participant's breast tissue due to the fact that there is a prognostic relationship between breast density and cancer risk. In general, it is known in the art that the radiographical density of a breast illustrated within a mammogram may vary due to differences in the amount of fat, connective tissues, and epithelial tissues that are present. For example, because fibroglandular and connective tissues (i.e. glands, ducts, and fibers) have a relatively high x-ray attenuation, fibroglandular and connective tissues may appear to be radiographically dense/light on radiographic films. By contrast, fat has a relatively low x-ray attenuation and therefore appears to be the least radiographically dense/dark, when compared to the remaining breast tissue. Because of the distinct differences in x-ray attenuation between fat and fibroglandular tissue, segmentation of fibroglandular tissue from the rest of the breast is possible.

A known breast density estimation standard may be based upon a four-category Breast Imaging Reporting and Data Systems (BI-RADS) lexicon. Upon visually assessing a mammogram, a radiologist may classify the radiographical image of the breast into one of four BI-RADS compositional categories defined as: 1: Fatty, 2: Scattered, 3: Heterogeneous, and 4: Dense. Women whose breasts are categorized in the BI-RADS 4/densest breast category are four-to-six times more likely to develop breast cancer than those categorized as BI-RADS 1/fatty.

Because the above standard in breast density estimation involves a radiologist's visual assessment of a mammogram, this assessment is subjective and relies on the perception of the radiologist. While such a subjective density classification is quick to use and widely employed, it has been proven to be limited due to considerable intra- and inter-reader variability of a radiologist.

Further, as also known in the art, the use of mammography is not ideal because of the associated radiation exposure to the participant that is undergoing breast evaluation Even further, a mammogram is a two-dimensional projection which, by definition, does not provide an accurate, three-dimensional volumetric estimation of the breast density due to the tissue thickness not being taken into account. Even further, it is also known that women are apprehensive about mammography due to the uncomfortable compression of the breast associated with the scan.

Accordingly, there is a need in the art for an improved method and apparatus for determining breast density. In an embodiment, the novel method and apparatus is a non-ionizing method and apparatus. In an embodiment, the determined breast density may be utilized for assessing cancer risk.

Further, because the novel methodology yields parameters that are associated with high breast density, which, in turn, may be associated with increased breast cancer risk, it will be appreciated that data arising from the novel methodology may be utilized to assess cancer risk directly without the intermediate step of determining breast density.

Yet even further, by identifying women having high breast density, further preventative measures can be implemented.

BRIEF DESCRIPTION OF THE DRAWINGS

The disclosure will now be described, by way of example, with reference to the accompanying drawings, in which:

FIGS. 8A-8F each illustrates a graphical representation of a lesion associated with breast tissue over time based upon acoustic parameters.

DETAILED DESCRIPTION OF THE INVENTION

The Figures illustrate an exemplary embodiment of a method and apparatus for determining breast density and assessing cancer risk utilizing acoustic parameters in accordance with an embodiment of the invention. Based on the foregoing, it is to be generally understood that the nomenclature used herein is simply for convenience and the terms used to describe the invention should be given the broadest meaning by one of ordinary skill in the art. Further, although an embodiment of the invention described in the foregoing disclosure is related to the analysis of breast tissue, it will be appreciated that the invention is not meant to be limited to breast tissue; for example, it will be appreciated that the invention may be utilized to analyze organ tissue, such as, for example, a liver. As such, the foregoing methodologies disclosed in the foregoing disclosure may be utilized to assess the risk of, for example, cancer of the liver.

I. Embodiment of an Apparatus

Figure 1:
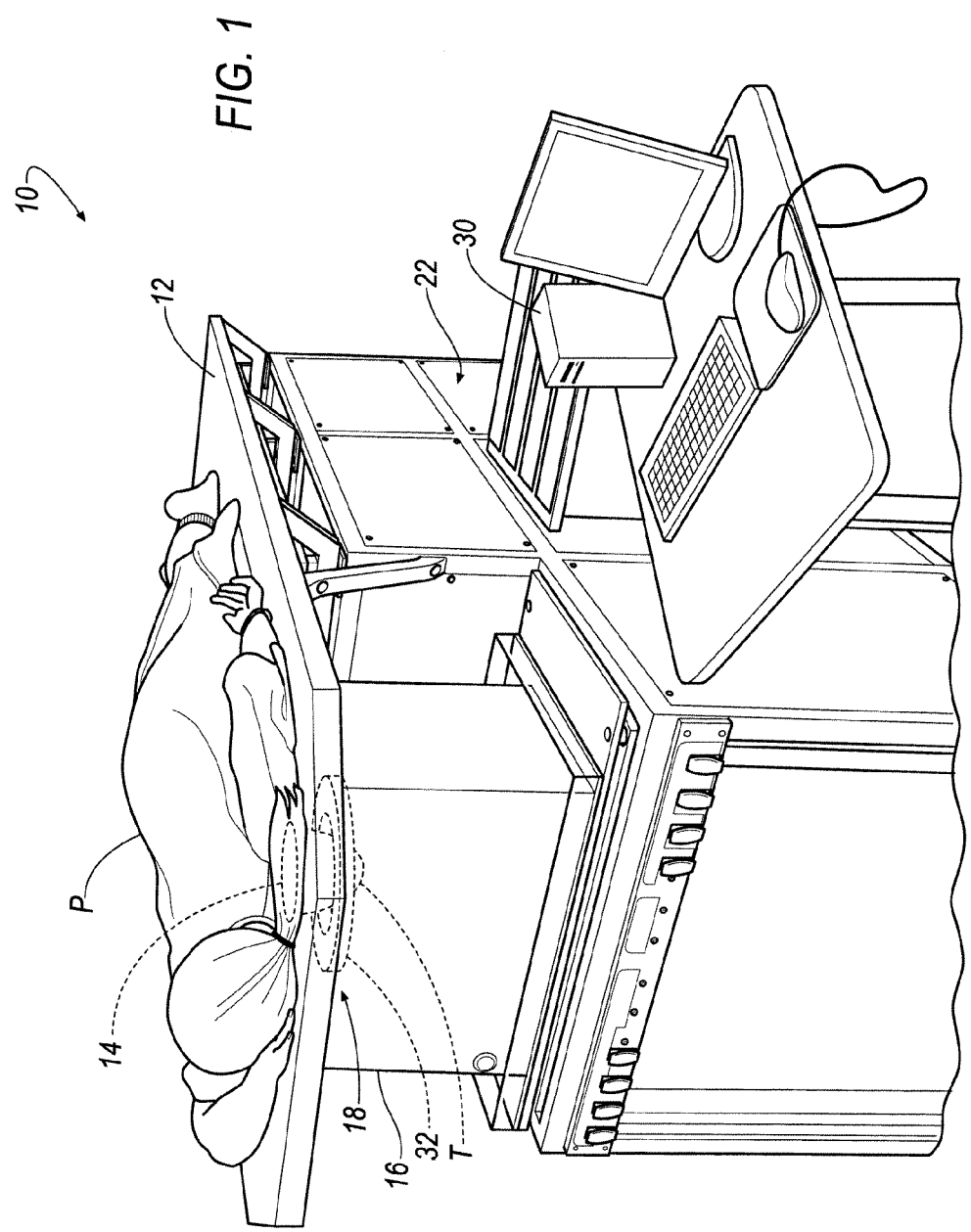
FIG. 1 is an environmental view of a non-ionizing, non-compressing, volumetric ultrasound tomography apparatus in accordance with an exemplary embodiment of the invention.

Referring to FIG. 1, an environmental view of a non-ionizing, non-compressing, volumetric ultrasound tomography apparatus 10 is shown according to an embodiment. According to an embodiment, the apparatus 10 includes a platform 12 having an opening 14 and a tank 16 having an imaging device 18 disposed in the tank 16.

Because the apparatus 10 utilizes ultrasound to analyze the tissue, T, there is no ionizing radiation exposure to the patient, P. In addition, because the tissue is immersed in a fluid within the tank 16, there is no compression of the tissue, T, which may otherwise cause discomfort to the patient, P. Even further, it will be appreciated that the apparatus 10 provides a volumetric, three-dimensional analysis of the tissue, T, as opposed to a less accurate, two-dimensional analysis of the tissue, T. Finally, it will be appreciated that the time it takes for apparatus 10 to scan a breast tissue volume is typically less than 90 seconds.

In an embodiment, the patient, P, is a female, and the tissue, T, being analyzed is breast tissue. However, it will be appreciated that the patient, P, being examined is not limited to being a female, and, the tissue, T, being scrutinized is not limited to breast tissue.

In operation and as shown in FIG. 1, the patient, P, is situated in a face-down position on the platform 12 such that the breast tissue, T, is inserted through the opening 14 and into the tank 16. As illustrated, the opening 14 is substantially aligned with the location of the tank 16, which is located under the platform 12, relative the patient, P. Once inserted through the opening 14, the breast tissue, T, is immersed in fluid within the tank 16.

Figure 2:
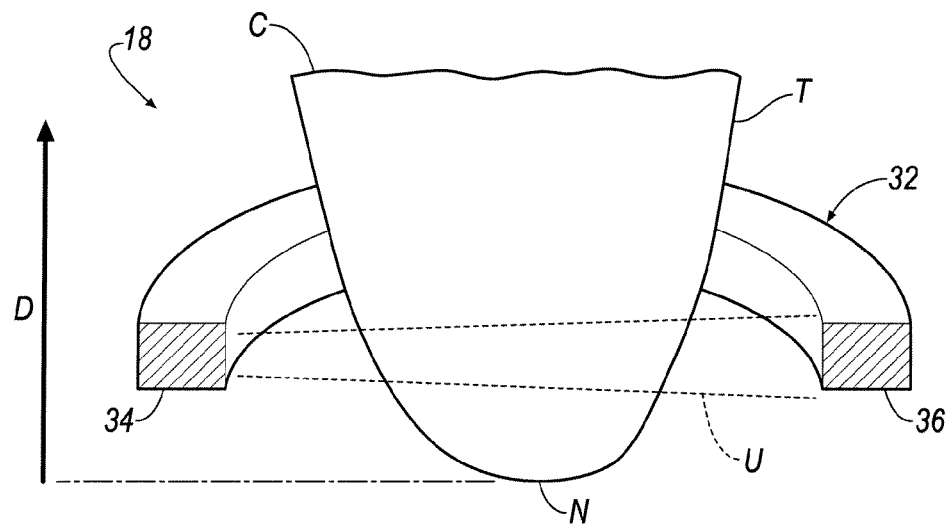
FIG. 2 is a perspective, cross-sectional view of an ultrasound transducer ring of the ultrasound tomography apparatus of FIG. 1 relative a breast in accordance with an exemplary embodiment of the invention.

Referring to FIG. 2, the imaging device 18 is shown according to an embodiment. The imaging device 18 may be an ultrasound tomography device comprising a transducer ring 32. As shown in FIG. 1, the transducer ring 32 of the imaging device 18 is immersed in the fluid. As is shown, the transducer ring 32 includes a transmitter end 34 and a receiver end 36.

According to an embodiment, the transmitter end 34 and receiver end 36 may be constructed from any desirable material, such as, for example, an array of piezoelectric elements, an array of ceramic elements, an array of electromechanical elements, an array of magnetostrictive elements, or the like. Even further, in an embodiment, it will be appreciated that the array may be static, a stationary pair, a rotated pair, or the like. In an embodiment, the array may comprise a two-dimensional array, or, alternatively, a three-dimensional array that may be translated along different planes to enable three-dimensional data collecting, which is described in greater detail below.

In an embodiment, an ultrasound caliper device including a transmitting end and receiving end, can also be used in a substantially similar manner as the transducer ring 32 in order to collect data. If an ultrasound caliper is utilized, acoustic parameters can be obtained and evaluated without the construction of a graphical image. Further, the use of an ultrasound caliper provides a simple, hand-held device and therefore eliminates the use of a relatively larger tank 16 including, for example, a water bath.

Referring to FIGS. 1 and 2, once the breast tissue, T, is inserted into the tank 16, the breast tissue, T, is circumscribed by the transducer ring 32. Thus, ultrasound analysis of the breast tissue, T, may be conducted by transmitting sound waves, U, from the transmitter end 34 to the receiver end 36 by way of the fluid and breast tissue, T, disposed within the tank 16.

To obtain a volumetric, three-dimensional analysis of the breast tissue, T, the transducer ring 32 is initialized to a start position within the tank 16. Once initialized to the desired starting position, the sound-waves, U, are emitted as the transducer ring 32 moves in a direction according to the arrow, D, toward the platform 12/chest, C, of the patient, P, to an end position. The fluid, which may be, for example, water, is known to have well-defined sound speed parameters that serve as both a coupling medium and a matching layer between the breast tissue, T, and the transducer elements 34, 36.

Although the above-disclosed embodiment is described to include an apparatus 10 having a tank 16 holding a fluid, it will be appreciated that the invention is not limited to the use of the apparatus 10 for obtaining tissue data of a breast. For example, coupling fluids other than water, such as, for example, acoustic gels, may be applied to an outer surface of the breast; and, in an embodiment, a transducer may directly contact the breast by way of the acoustic gel. In another embodiment, a single transducer in conjunction with acoustic mirrors may also be utilized instead of the apparatus 10. A further alternative embodiment may include measurements in the time domain such that collected data from one or more transducers is not related to imaging data associated with the apparatus 10.

II. Determining Breast Density

In an embodiment, the sound waves, U, may be utilized to determine whole-breast acoustic measures. In an embodiment, the sounds waves, U, are utilized to determine an average whole breast acoustic sound speed velocity. The average whole breast acoustic sound speed velocity may then be utilized as an indicator of the density of the breast tissue, T.

In an embodiment, the speed of the sound waves, U, is based on signals transmitted through the breast tissue, T, and are used to generate graphical maps of the sound speed distribution. In an embodiment, the sound speed may be provided in a scale of, for example, meters-per-second (m/s). In another embodiment, graphical maps of sound speed distribution are not created such that a sound speed measurement, calculation or the like representing an entire breast may be provided. In an embodiment, the sound speed measurement, calculation or the like may be utilized as a factor for assessing cancer risk.

Figure 3:
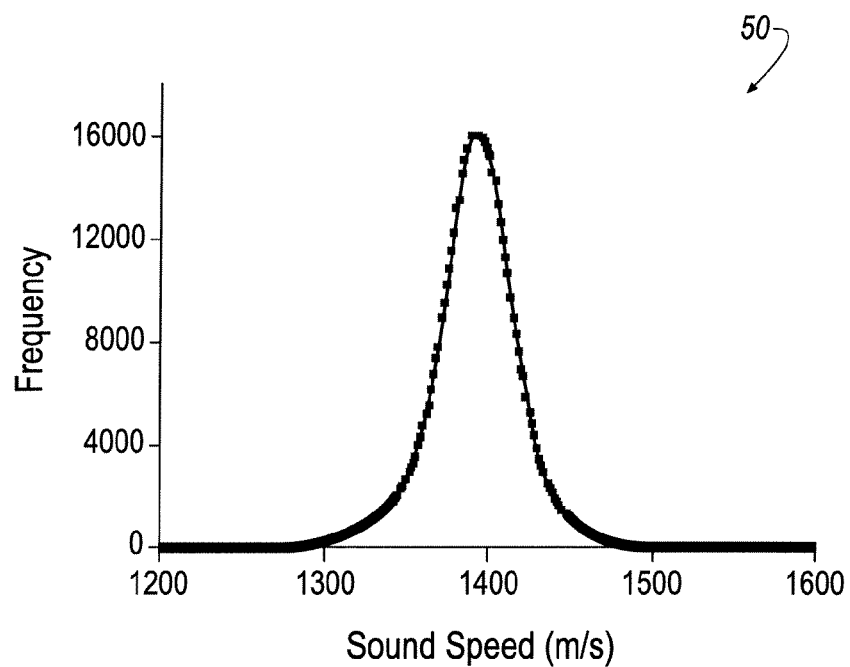
FIG. 3 is a tissue sound speed frequency histogram of a subject obtained from the apparatus of FIG. 1.

In an embodiment, whole breast acoustic velocity may be defined as a global sound speed measure obtained from a sound speed histogram 50 (see, e.g., FIG. 3), which is developed from tomograms that are produced, in an embodiment, by the apparatus 10. Referring to Equation 1 below, under the assumption that the tissue, T, is fluid-like, the speed of sound (V) has the following relationship to an elastic constant (c) and material density (p) of the material through which the sound waves, U, travel:

$$V = \sqrt{\frac{c}{p}} \qquad (1)$$

From this relationship, the average velocity 52 (see, e.g. FIG. 4) through tissue, T, would be related to the breast density and elasticity. Water, which has similar properties to tissue, T, has a bulk elastic constant of $2.2 \times 10^9$ N/m$^2$. In vitro and in vivo data both support the relationship of increased sound speed with increased density of material.

To provide the histograms 50, image stacks are created for each segment of the patient's breast as the transducer ring 32 moved from its initialized start position to its end position. Because an image stack corresponds to the entire breast volume, the histograms 50 represent the statistical distribution of all sound speed voxels within that particular breast. From the histogram 50, an overall mean sound speed value for each breast is obtained to provide a single-value estimate of the volumetric average of the sound speed velocity 52 of the whole breast.

It will be appreciated, however, that measurements of an overall mean is not intended to limit the present invention and that other measures may be utilized. For example, other measures may include, but are not limited to a median, mode, midrange, skewness, kurtosis, or the like.

It will be appreciated that an overall sound speed is not meant to limit the present invention and that other measures of acoustical data may be utilized. For example, other acoustical data may include, but are not limited to attenuation, reflection, elasticity, or the like. Also, derivations of acoustical properties other than measures of central tendency may be used to derive a whole breast density measure. Examples could include parameters such as texture (2D or 3D, skewness, kurtosis, etc.) and pattern (fractal dimension, lacunarity, etc.). Even further, data integration could also be used for whole breast density acoustical measures, such as combining features from several temporal scans, different acoustical parameters, etc.

Figure 4:
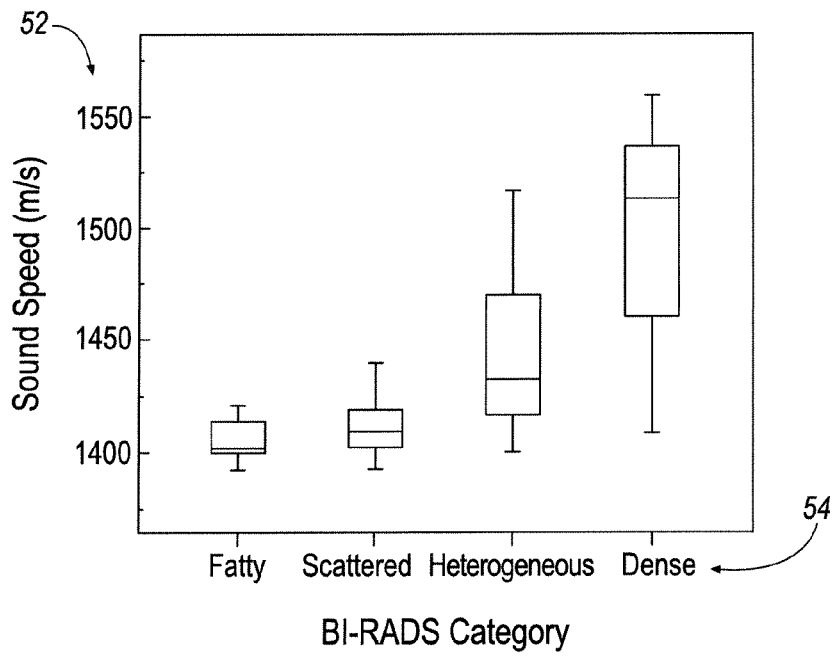
FIG. 4 is a plot of mean tissue sound speed for a group of subjects according to a BI-RADS compositional categorization.

Referring to FIG. 4, as a basis to correlate breast density and the average acoustic sound speed velocity 52, a sampling of average sound speed histograms 50 were arranged against corresponding qualitative BI-RADS breast density measures 54 for each subject of the sampled population. As is known in the art, BI-RADS compositional categories are a known breast density estimation standard (i.e., classification in BI-RADS: 1-3 means there is a lesser cancer risk than a classification of BI-RADS:4). The use of BI-RADS in FIG. 4 is for comparative purposes to illustrate the inventive concept of utilizing non-ionizing acoustics to quantify a cancer risk assessment of a biological tissue such as, for example, breast tissue, T.

Accordingly, to establish the data shown in FIG. 4, each patient, P, in the sampled population were subjected to an acoustic signal such that whole-breast sound speed data could be measured and analyzed for obtaining an acoustic measure of each patient's breast tissue, T. Prior to or after obtaining the acoustic measure, a BI-RADS classification for each patient was also established. Accordingly, as illustrated in FIG. 4, data for the entire sampled population was compiled. It can be seen that as the average acoustic sound speed velocity 52 of each patient's breast tissue, T, increases, there is also an increase, in a corresponding fashion, with a radiologist's qualitative assessment of the BI-RADS density of each subject patient, P.

In an embodiment, the relationships of the data shown in FIG. 4 are expressed as follows. According to an embodiment, average volumetric sound speed velocities 52 ranging between approximately 1400-1415 m/s relate to a fatty (BI-RADS: 1) categorization. According to an embodiment, average volumetric sound speed velocities 52 ranging between approximately 1405-1420 m/s relate to a scattered (BI-RADS: 2) categorization. According to an embodiment, average volumetric sound speed velocities 52 ranging between approximately 1420-1465 m/s relate to a heterogeneous (BI-RADS: 3) categorization. According to an embodiment, average volumetric sound speed velocities 52 ranging between approximately 1460-1575 m/s relate to a dense (BI-RADS: 4) categorization.

It will be appreciated that by using the above-described data associated with FIG. 4 as a frame of reference, sound speed threshold values can be determined and utilized alone (without determining density of breast tissue, T) to identify women who are at increased breast cancer risk. To serve as an example, if a patient's breast tissue, T, is defined to have a sound speed measure of, for example, 1402 m/s, the measure falls into the range of 1400-1415 m/s, and, as such, the patient, P, may be said to have a lesser risk of developing breast cancer in the future due to the fact that the 1402 m/s measure falls in the range of 1400-1415 m/s, which is associated with a fatty/BI-RADS: 1 categorization.

Thus, the four sound speed ranges described above may establish, in an embodiment, the basis of a cancer risk model such that a sound speed measure falling into the range of 1460-1575 m/s may be said to have a greatest risk of developing breast cancer than sound speed measures in the ranges of 1420-1465 m/s, 1405-1420 m/s, and 1400-1415 m/s. Accordingly, by obtaining a measure (e.g., sound speed) and comparing the measured value against the above ranges, a quantified risk assessment may be obtained.

It can be appreciated that the basis of a breast cancer risk evaluation model using acoustic parameters is not limited to comparisons with BI-RADS compositional categories, and instead, more quantitative evaluation methods can be considered (i.e. computer-assisted segmentation of mammograms using interactive thresholding or automated segmentation). Further, it can be appreciated that a breast cancer risk evaluation model can be developed independent of any association with other breast density evaluation techniques.

It will be appreciated, however, that although sound speed is described above, a measured distribution of an acoustic signal is not limited to sound speed; for example, the measured distribution of acoustic signals may also be applied to attenuation, reflectivity, elasticity and the like. Further, the cancer risk model may be further refined by also applying additional data to, for example, the measured sound speed. In an embodiment, the additional data may include, for example, one or more of age, menopausal status, age at menarche, parity, age at first birth, number of first and second degree relatives with breast cancer, prior breast biopsies, hormonal usage, history of atypical hyperplasia, or history of lobular carcinoma in situ, and the like.

III. Determining Breast Density Using a Tissue Volume Separator

Figure 5:
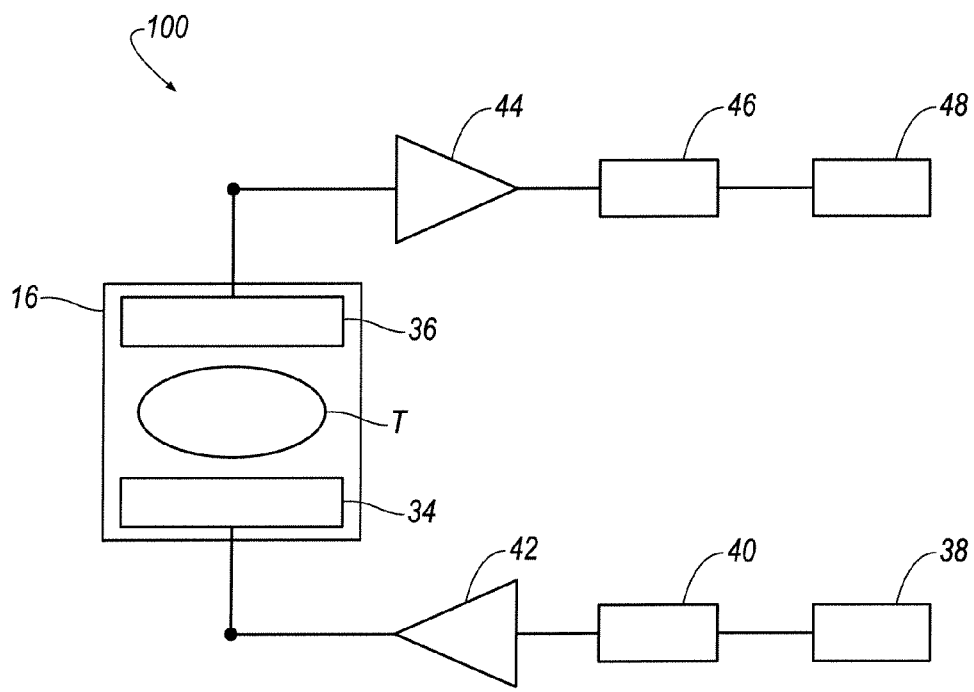
FIG. 5 is a block diagram of an apparatus for determining ultrasound percent density in accordance with an exemplary embodiment of the invention.

Referring now to FIG. 5, a block diagram 100 for a tissue volume separator from acoustic data provided by the apparatus 10 is shown generally at 100 according to an embodiment. The block diagram generally includes a waveform generator 38, a digital-to-analog converter 40, an acoustic transmit amplifier 42, the transmitter end 34, the receiver end 36, an acoustic receive amplifier 44, an analog-to-digital converter 46, and tissue volume separator value generator 48.

Functionally, the waveform generator 38 creates a series of digital signals. The digital signals are sequentially sent to the digital-to-analog converter 40 that converts each signal to a corresponding analog out-put signal which is then amplified by the transmit amplifier 42. The amplified signal drives the transmitter end 34, which converts the electrical analog signal into an acoustical signal, which propagates through the fluid in the tank 16 to the receiver end 36. The receiver end 36 converts the acoustical signal back into an electrical analog received signal, which may be amplified by a receive amplifier 44. The received signal may be digitized by the analog-to-digital converter 46.

The sampling rate of the analog-to-digital converter 46 can be set to digitize the analog signal at the Nyquist (or other) rate corresponding to the frequency used to drive the transducers 34, 36. The resulting digital data stream may be stored in the tissue volume separator 48, which may include a digital storage system in the form a random access memory, a hard drive, or the like. It will be appreciated that the tissue volume separator may be a stand-alone device, or, alternatively, be incorporated in the electronics 22, or, alternatively be incorporated in the central processing unit 30.

To determine the tissue volume separator results of the breast tissue, T, the processor of the breast density factor 48 is concerned with breast sound speed. According to an embodiment as seen in Equation 2 below, a tissue density factor, TDF, can be defined by:

$$TDF = \frac{High\_Sound\_Speed\_Volume}{Total\_Breast\_Volume} \quad (2)$$

The denominator (i.e., Total Breast Volume) is further defined as the total (summed) integrated areas of breast sound speed tomograms. The numerator (i.e., High Sound Speed Volume Data) is further defined as the integrated area of sound speed regions from the sound speed tomograms that are considered to be of high sound speed value. The can be determined by the areas exceeding a sound speed threshold value. This threshold for determining high sound speed is not meant to limit the present invention and that other techniques used to segment higher sound speed regions may be utilized. For example, other techniques may include, but are not limited to semi-automated or automated: k-means or fuzzy clustering, segmentation in the frequency domain or time domain, artificial neural networks, or the like. Further, the TDF can be determined from data arising directly from a three-dimensional (3D) volume as opposed to a stack of two dimensional (2D) tomograms.

It can be appreciated that using this methodology, sound speed threshold values can be determined and applied to an entire population, thereby associating TDF value of a subject to identify the likelihood of breast cancer risk. Similarly, tissues other than fatty and fibroglandular may be further segmented by volumetric assessment of other ultrasound parameters. In an embodiment, it will be appreciated that the TDF is not restricted to a ratio, but also, an absolute integrated area of dense tissue and total breast tissue as indicators of breast cancer risk.

Figure 6A:
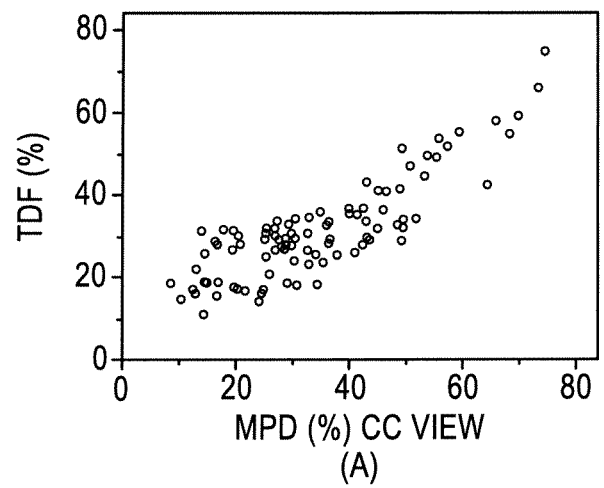
FIG. 6A is a plot of tissue density factor (TDF) according to quantitatively obtained mammographic percent density.
Figure 6B:
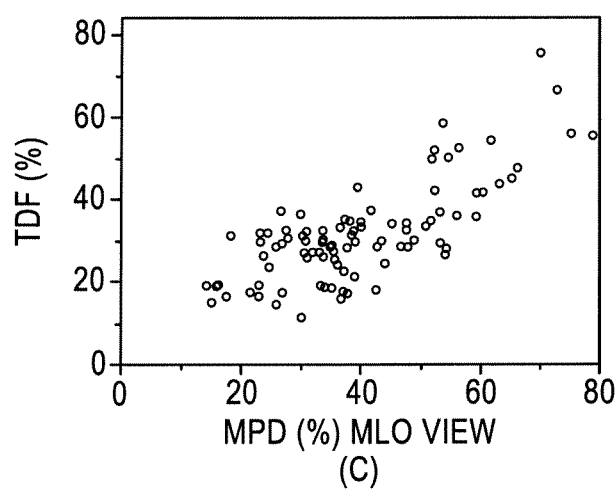
FIG. 6B is a plot of tissue density factor (TDF) according to quantitatively obtained mammographic percent density.

Referring to FIGS. 6A and 6B, as a basis to correlate TDF and breast density, the TDF is shown along the y-axis and quantitative mammographic percent density using semi-automated segmentation routines is shown along the x-axis. The TDF was calculated according to Equation 2 above for a plurality of patients and the results are correlated to a corresponding quantitative mammographic percent density (MPD) measures for each patient of the plurality of patients. For illustrative purposes, FIG. 6A provides an MPD for the craniocaudal (CC) view and FIG. 6B provides an MPD for the mediolateral oblique (MLO) (MLO) view. In general, FIGS. 6A and 6B provides evidence that as TDF of the breast tissue, T, increases, the MPD increases in a corresponding fashion.

It will be appreciated that, similar to providing several different volumetric distributions of imaging data, the associated tissue characterizations and assorted tissue types can be displayed in multiple different distributions. While sound speed has been currently used to separate fatty from parenchymal breast tissues for volumetric density estimates, other imaging data (such as attenuation, reflectivity, elasticity, etc.) may allow further volumetric separation of cystic areas, and benign and malignant tumors from the current separation of fatty and parenchymal tissue by sound speed alone.

IV. Applications of Acoustic and TDF Measurements of the Breast

Multiple measurements of the breast can be conducted in space in a repeated fashion by positioning the transducer ring 32 and discretely measuring the breast tissue, T, in two-dimensional cycles until full, three-dimensional coverage of the breast tissue, T, is achieved. As such, discrete, two-dimensional measurements of the breast tissue, T, may be obtained to provide coverage of the breast tissue, T, at different cross-sections to simulate a three-dimensional analysis of the breast tissue, T, by 'stacking' a plurality of discrete, two-dimensional measurements. Although it is possible to 'stack' a plurality of discrete, two-dimensional measurements to provide a three-dimensional measurement, it will be appreciated that a direct three-dimensional measurement with a two-dimensional array is also possible.

Figures 7A, 7B, 7C, 7D:
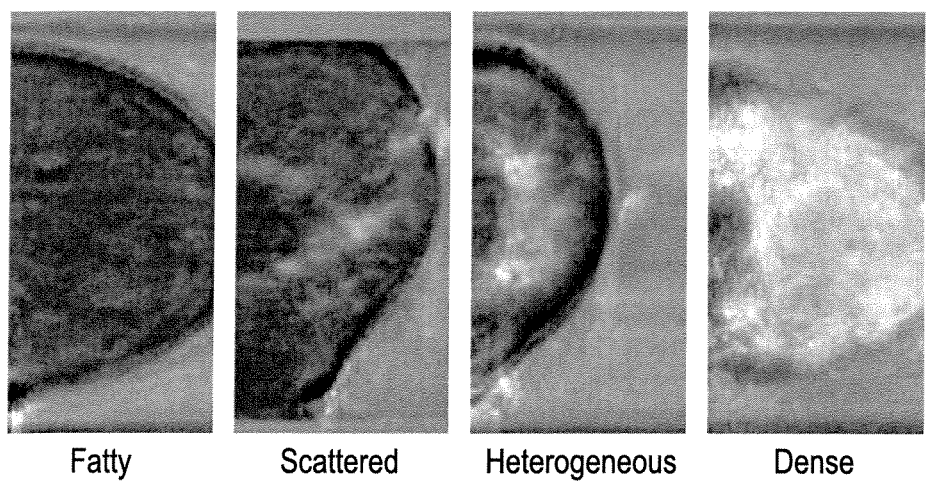
FIGS. 7A-7D each depict a graphical representation of intensity projections of three-dimensional sound speed data for a typical breast from each BI-RADS compositional category (1: fatty to 4: dense), wherein the white regions demonstrate high sound speed values relative to the darker lower sound speed regions.

It will be appreciated that having three-dimensional reconstructions of the breast also can allow for 2D or 3D projection images of the acoustical parameters such that a direct comparison to mammography can be made. In an embodiment, as shown in FIGS. 7A-7D, maximum intensity projections of graphical sound speed maps are shown such that exemplar images of the four BI-RADS categorizes are represented. As seen in FIG. 7A, for example, a sound speed map of a BI-RADS 1/fatty tissue, T, is shown. As seen in FIG. 7B, for example, a sound speed map of a BI-RADS2/scattered tissue, T, is shown. As seen in FIG. 7C, for example, a sound speed map of a BI-RADs 3/heterogeneous tissue, T, is shown. As seen in FIG. 7D, for example, a sound speed map of a BI-RADS 4/dense tissue, T, is shown. Here, the white regions demonstrate high sound speed values relative to the darker lower sound speed regions. It will be appreciated, however, that although maximum intensity projections of three-dimensional sound speed reconstruction is provided in each of FIGS. 7A-7D, graphical representations may be extended to different projections and acoustical parameters other than sound speed.

In an embodiment, the sound speed may be estimated either through direct measurement (e.g., with a transducer pair or set of ultrasound calipers). The direct measurement of sound speed through the tissue, T, is independent of reconstructed images such that the sound speed is determined directly from the timing of the arrival of the pulses without requiring the complexity of any imaging. In another embodiment, a series of sound speed tomographic images can be formed and used to obtain the volume averaged sound speed.

According to an embodiment, the stored data may be analyzed by a software program that is stored, in an embodiment, within the tissue volume separator 48 to determine various acoustic parameters associated with the interaction of the sound waves, U, with the breast tissue, T. The novel methodology associated with the software can be used to categorize breast tissue density and evaluate parameters such as sound speed, attenuation, reflectivity, elasticity, and TDF. It can be appreciated that this software can also be used to provide a combination of such parameters that may best distinguish women with elevated breast density, and, as such, an increased risk of breast cancer. An extension of such software may include the development of a breast cancer risk assessment model to incorporate other risk factors such as age, menopausal status, age at menarche, parity, hormonal usage, age at first birth, number of first and second degree relatives with breast cancer, prior breast biopsies, history of atypical hyperplasia, or history of lobular carcinoma in situ using any number of aforementioned acoustic parameters.

Using aforementioned measurements of the breast, a new classification scheme may be developed to characterize breast density using one or more acoustic parameters, TDF, or any combination thereof. It will be appreciated that due to the multitude of acoustic parameters available and the ability to measure them repeatedly, a more quantitative breast density classification scheme may be realized than currently employed using the mammographic BI-RADS Categories.

Finally, it will be appreciated that many alternative applications to volumetric tissue evaluation over time may be conducted rather than evaluating breast density over time. As noted, a diagnostic value is anticipated from volumetric tissue assessments in response to changes during the exam (e.g., temperature, shape, pressure, intravenous contrasts). Similarly, as seen in FIGS. 8A-8F, malignant tumor responses over time show volume reduction capabilities by utilizing sound speed to analyze the breast tissue, T. In an embodiment, the successive images in FIGS. 8A-8F are taken approximately two weeks apart for a patient undergoing chemotherapy. In an embodiment, changes in sound speed, tumor volume, and other acoustical properties can be tracked and estimated using a tissue volume separator. Accordingly, the invention may be utilized to analyze tumor volume reduction over time as a patient undergoes, for example, chemotherapy, radiation therapy, surgery or the like. In another embodiment, for example in benign tumors and fibrocystic breasts, the effectiveness of dietary and chemoprevention interventions maybe quantifiable in terms of density and acoustic property changes.

V. Benefits of Determining a Breast Density by Utilizing Acoustics

It is known that women under the age of 40 do not routinely undergo mammographic screening for breast cancer because the benefit of receiving mammographic examinations does not outweigh the risk associated with the exposure to ionizing radiation. The processes disclosed herein for determining breast density are conducted without exposing the subject to harmful ionizing radiation, and accordingly allow for risk-free screening and the establishment of baselines at an earlier age. Moreover, the present invention presents and objective approach for assessing present and future cancer risk. This is in contrast to the subjective nature of interpreting mammograms.

Even further, because the tissue undergoing examination, T, is not compressed in any of the methodologies associated with the present invention, the evaluation of the tissue, T, is conducted when the breast tissue is in a non-compressed, natural shape thereby rendering a more accurate representation of the spatial distribution of fibroglandular and fat tissues. Further, by not utilizing a compression technique, women may be more likely to respond favorably to the comfort of the scan, particularly when comparing the embodiments of the present invention to mammography.

In obtaining the breast density by way of the present methodologies, a reduced amount of time may be employed when evaluating a subject's tissue, T; the examination may take as little as five minutes to set-up and one minute to conduct. As a result of knowing one's breast tissue density, preventative measures may be taken, as the relative risk of breast cancer increases with increased breast density. Preventative measures may include, for example, the screening of such subjects at a younger age (e.g., women who are not of mammographic age, such as women that are younger than 40 years old) and/or the screening of such subjects with a greater than annual frequency. In addition, knowing one's tissue density may justify the use of chemoprevention methods. Chemoprevention methods may include, for example, dietary intervention or use of Tamoxifen.

In addition, by knowing one's acoustical or TDF measures, the known tissue density may be utilized as a baseline value for subsequent comparison over time. For example, if a subsequent screening determined breast density has increased in view of one's previous/baseline breast density, the subject may be advised to undergo earlier/preventative screenings, which may not otherwise be suggested without the knowledge of the change in breast density from the baseline.

Volumetric changes over time in response to temporal alterations of the ultrasound parameters provide further potential tissue characterization. Volumetric tissue responses can be measured during a single or multiple scans. Parameters which may be altered during a single scan session may include, but are not limited to: temperature, shape, pressure, and vascular content. Further, it will be appreciated that these more immediate volumetric changes may include all or a portion of the scanned volume. Changes in volumetric ultrasound parameters affecting vascular content may be in response to any variety of intravenous or interstitial agents which change the reflectivity, sound speed, attenuation, elasticity, etc. Volumetric parameters which may be altered during multiple scan session include, but are not limited to, interval interventions, such as: responses to chemotherapy, chemoprevention, dietary changes, radiation treatment, tumor ablations or other surgical interventions.

Even further, it will be appreciated that many alternative applications of the present invention may also be made available. For example, the breast tissue density could be monitored in response to treatments such as, for example, soy isoflavones, dietary interventions, hormone-replacement therapy, and the like. In addition, the acoustical parameters and TDF could evaluate breast density over the phases of one's menstrual cycle, which may assist in determining the ideal time span to evaluate the breast. Alternatively, the breast density could be used to determine the natural variance of breast density for each patient.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

What is claimed is:

1. A method, comprising:
   transmitting an acoustic signal through a breast tissue volume;
   measuring, throughout the breast tissue volume, a distribution of one or more acoustic parameters comprising sound speed based upon an analysis of the acoustic signal transmitted through the breast tissue volume;
   obtaining an average whole breast sound speed velocity based upon at least a measured distribution of sound speed; and
   quantifying present or future cancer risk based upon a comparison between the average whole breast sound speed velocity and one or more of the following BI-RADS breast density measures:

a fatty BI-RADS: 1 categorization if the average whole breast sound speed velocity is substantially between 1400-1415 m/s;
a scattered BI-RADS: 2 categorization if the average whole breast sound speed velocity is substantially between 1405-1420 m/s;
a heterogeneous BI-RADS: 3 categorization if the average whole breast sound speed velocity is substantially between 1420-1465 m/s; and
a dense BI-RADS: 4 categorization if the average whole breast sound speed velocity is substantially between 1460-1575 m/s.

2. The method according to claim 1, further comprising: utilizing a tissue volume separator to conduct the measuring step, wherein the tissue volume separator further conducts the step of segmenting data for conducting the measuring step.

3. The method according to claim 2, wherein obtaining an average whole breast sound speed velocity comprises dividing a segmented volume of the breast tissue volume, segmented based on an acoustic parameter of the one or more acoustic parameters, by a total breast volume.

4. The method according to claim 3, wherein segmenting data comprises dividing a volume of tissue having a sound speed exceeding a sound speed threshold value by the total breast volume.

5. The method according to claim 1, wherein the one or more acoustic parameters comprise attenuation.

6. The method according to claim 1, wherein obtaining an average whole breast sound speed velocity comprises obtaining a statistical measure of central tendency.

7. The method according to claim 6, wherein the statistical measure of central tendency comprises a mean, mode, median, range, or standard deviation of one or more of sound speed and attenuation obtained from analyzing the acoustic signal.

8. The method according to claim 1, wherein the acoustic signal comprises a sequential series of waves.

9. The method according to claim 1, wherein the acoustic signal comprises a sequential series of pulses.

10. The method according to claim 1, wherein obtaining the average whole breast sound speed velocity further comprises:
developing at least one average sound speed histogram arising from the measured distribution of sound speed; and
obtaining the average whole breast sound speed velocity based on the at least one average sound speed histogram.

11. A method, comprising the steps of:
transmitting an acoustic signal through a volume of biological tissue;
measuring, throughout the volume of biological tissue, a distribution of at least one acoustic parameter comprising one or more of sound speed and attenuation by analyzing the acoustic signal transmitted through the volume of biological tissue;
obtaining an average sound speed velocity measure of the volume of biological tissue based upon the measured sound speed; and
quantifying present or future cancer risk based upon a comparison between the average sound speed velocity measure and one or more of the following BI-RADS breast density measures:
a fatty BI-RADS: 1 categorization if the average sound speed velocity measure is substantially between 1400-1415 m/s;
a scattered BI-RADS: 2 categorization if the average sound speed velocity measure is substantially between 1405-1420 m/s;
a heterogeneous BI-RADS: 3 categorization if the average sound speed velocity measure is substantially between 1420-1465 m/s; and
a dense BI-RADS: 4 categorization if the average sound speed velocity measure is substantially between 1460-1575 m/s.

12. The method according to claim 11, wherein the quantifying step is conducted without obtaining a measure of biological tissue density.

13. The method according to claim 12, further comprising: applying one or more of an age, menopausal status, age at menarche, parity, age at first birth, number of first and second degrees relatives with breast cancer, prior breast biopsies, hormonal usage, history of atypical hyperplasia, or history of lobular carcinoma in situ of a host subject of the biological tissue with the obtained measure to further refine the quantifying step.

14. The method according to claim 12, wherein the biological tissue is breast tissue.

15. The method according to claim 12, wherein the biological tissue is organ tissue, wherein the organ tissue is liver tissue.

16. The method according to claim 11, wherein the obtained measure of the biological tissue is a statistical measure of central tendency used for assessing density of the biological tissue.

17. The method according to claim 16, further comprising: applying one or more of an age, menopausal status, age at menarche, parity, age at first birth, number of first and second degrees relatives with breast cancer, prior breast biopsies, hormonal usage, history of atypical hyperplasia, or history of lobular carcinoma in situ of a host subject of the biological tissue with the obtained measure to further refine the quantifying step.

18. The method according to claim 11, wherein the biological tissue is breast tissue.

19. The method according to claim 11, wherein the biological tissue is any organ tissue.

20. The method according to claim 11, wherein obtaining the average sound speed velocity measure further comprises:
developing at least one average sound speed histogram arising from the measured sound speed; and
obtaining the average whole breast sound speed velocity based on the at least one average sound speed histogram.

21. An apparatus, comprising:
a non-ionizing apparatus located proximate breast tissue, wherein the non-ionizing apparatus comprises a transducer configured to expose the breast tissue to an acoustic signal by transmitting the acoustic signal through the breast tissue;
a tissue volume separator coupled to the non-ionizing apparatus, wherein the tissue volume separator is configured to measure a distribution of one or more acoustic parameters comprising sound speed based upon an analysis of the acoustic signal;
a first module configured to obtain an average whole breast sound speed velocity based on the measured distribution of sound speed; and
a second module configured to quantify present of future cancer risk based upon a comparison between the average whole breast sound speed velocity and one or more of the following BI-RADS breast density measures:

a fatty BI-RADS: 1 categorization if the average whole breast sound speed velocity is substantially between 1400-1415 m/s;

a scattered BI-RADS: 2 categorization if the average whole breast sound speed velocity is substantially between 1405-1420 m/s;

a heterogeneous BI-RADS: 3 categorization if the average whole breast sound speed velocity is substantially between 1420-1465 m/s; and a dense BI-RADS: 4 categorization if the average whole breast sound speed velocity is substantially between 1460-1575 m/s.

22. The apparatus according to claim 21, wherein the non-ionizing apparatus comprises:
   a platform disposed substantially adjacent a tank, wherein the tank includes a fluid;
   means for inserting the breast tissue into the tank and proximate to the transducer;
   wherein the transducer is configured to transmit the acoustic signal through the breast tissue for receipt at the tissue volume separator.

23. The apparatus according to claim 21, wherein a coupling fluid is disposed upon the breast tissue, wherein the non-ionizing apparatus comprises:
   an ultrasound caliper disposed upon the coupling fluid and proximate to the breast tissue, wherein the ultrasound caliper comprises
   means for imparting the acoustic signal to the breast tissue for receipt at the tissue volume separator.

24. The apparatus according to claim 21, wherein the tissue volume separator comprises:
   an imaging device; and
      a waveform generator,
      a digital-to-analog converter connected to the waveform generator,
      an acoustic transmit amplifier connected to the digital-to-analog converter,
      wherein the acoustic transmit amplifier is connected to a transmitter end of the imaging device,
      a receive amplifier, wherein the receive amplifier is connected to a receiver end of the imaging device,
      an analog-to-digital converter connected to the receive amplifier, and
      a value generator connected to the analog-to-digital converter.

25. The apparatus according to claim 24, wherein the imaging device is an ultrasound tomography device defined, at least in part, by a transducer ring.

26. A method, comprising:
   transmitting an acoustic signal through a volume of biological tissue;
   measuring, throughout the volume of biological tissue, a distribution of at least one acoustic parameter including one or more of sound speed and attenuation by analyzing the transmitted acoustic signal; and
   quantifying present or future cancer risk by associating an average whole breast sound speed velocity with one or more of the following BI-RADS breast density measures:
      a fatty BI-RADS: 1 categorization if the average whole breast sound speed velocity ranges between approximately about 1400-1415 m/s;
      a scattered BI-RADS: 2 categorization if the average whole breast sound speed velocity ranges between approximately about 1405-1420 m/s;
      a heterogeneous BI-RADS: 3 categorization if the average whole breast sound speed velocity ranges between approximately about 1420-1465 m/s; and
      a dense BI-RADS: 4 categorization if the average whole breast sound speed velocity ranges between approximately about 1460-1575 m/s.

* * * * *